(12) United States Patent
Kawamura

(10) Patent No.: US 11,278,257 B2
(45) Date of Patent: Mar. 22, 2022

(54) DIAGNOSTIC AUXILIARY IMAGE GENERATION APPARATUS, DIAGNOSTIC AUXILIARY IMAGE GENERATION METHOD, AND DIAGNOSTIC AUXILIARY IMAGE GENERATION PROGRAM

(71) Applicant: FUJIFILM Corporation, Tokyo (JP)

(72) Inventor: Takahiro Kawamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1420 days.

(21) Appl. No.: 15/070,663

(22) Filed: Mar. 15, 2016

(65) Prior Publication Data

US 2016/0270753 A1 Sep. 22, 2016

(30) Foreign Application Priority Data

Mar. 20, 2015 (JP) .............................. JP2015-057329

(51) Int. Cl.
*A61B 6/00* (2006.01)
*G06T 7/00* (2017.01)

(52) U.S. Cl.
CPC ............ *A61B 6/5235* (2013.01); *A61B 6/461* (2013.01); *A61B 6/486* (2013.01); *A61B 6/503* (2013.01);
(Continued)

(58) Field of Classification Search
CPC .................................................. A61B 6/5235
See application file for complete search history.

(56) References Cited

U.S. PATENT DOCUMENTS 5,982,953 A * 11/1999 Yanagita ............... G06F 19/321
 348/580
7,454,965 B2 11/2008 Blossfeld et al.
(Continued)

FOREIGN PATENT DOCUMENTS

JP 2005-269214 A 9/2005
JP 2007-014435 A 1/2007

OTHER PUBLICATIONS

Nobuhiro Oda et al., "Development of Computerized System for Selection of Similar Images from Different Patients for Image Subtraction of Chest Radiographs", Biomedical Engineering, 2006, pp. 435-444, vol. 44, No. 3.

(Continued)

*Primary Examiner* — Rochelle D Turchen
(74) *Attorney, Agent, or Firm* — Sughrue Mion, PLLC

(57) ABSTRACT

In order to assist the interpretation of a radiation image in which an abnormality appears, the invention provides a diagnostic auxiliary image generation apparatus, a diagnostic auxiliary image generation method, and a non-transitory computer readable recording medium recorded with a diagnostic auxiliary image generation program for generating a diagnostic auxiliary image. In a case where a past radiation image is present, a temporal difference image generation unit generates and sets a temporal difference image as a diagnostic auxiliary image only in a case where the projected images of a diagnostic target radiation image and the past radiation image match each other. In a case where a past radiation image is not present or the projected images of a diagnostic target radiation image and a past radiation image do not match each other, a bone-suppressed image generation unit generates and sets a bone-suppressed image as a diagnostic auxiliary image.

26 Claims, 7 Drawing Sheets

(52) U.S. Cl.
CPC .............. *A61B 6/504* (2013.01); *A61B 6/505* (2013.01); *A61B 6/5205* (2013.01); *A61B 6/5217* (2013.01); *A61B 6/54* (2013.01); *G06T 7/0014* (2013.01); *G06T 2207/10116* (2013.01); *G06T 2207/30008* (2013.01); *G06T 2207/30061* (2013.01)

(56) References Cited

U.S. PATENT DOCUMENTS

| | | | | |
|---|---|---|---|---|
| 2009/0028403 | A1* | 1/2009 | Bar-Aviv | G06F 19/321 382/128 |
| 2010/0250275 | A1* | 9/2010 | Sakagawa | G16H 50/70 705/2 |
| 2010/0266188 | A1* | 10/2010 | Burns | G06T 7/30 382/132 |
| 2014/0015830 | A1* | 1/2014 | Hong | H04N 13/128 345/419 |
| 2015/0110380 | A1* | 4/2015 | Kobayashi | G06T 7/33 382/132 |

OTHER PUBLICATIONS

"Chest X-ray Screening Decision Manual", Complete Medical Examination and Determination Guidelines, Japan Society of Ningen Dock, Sep. 30, 2013, translation.

* cited by examiner

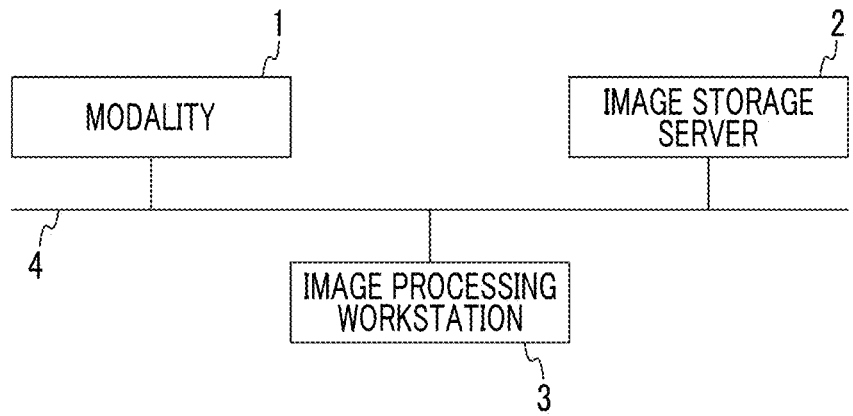
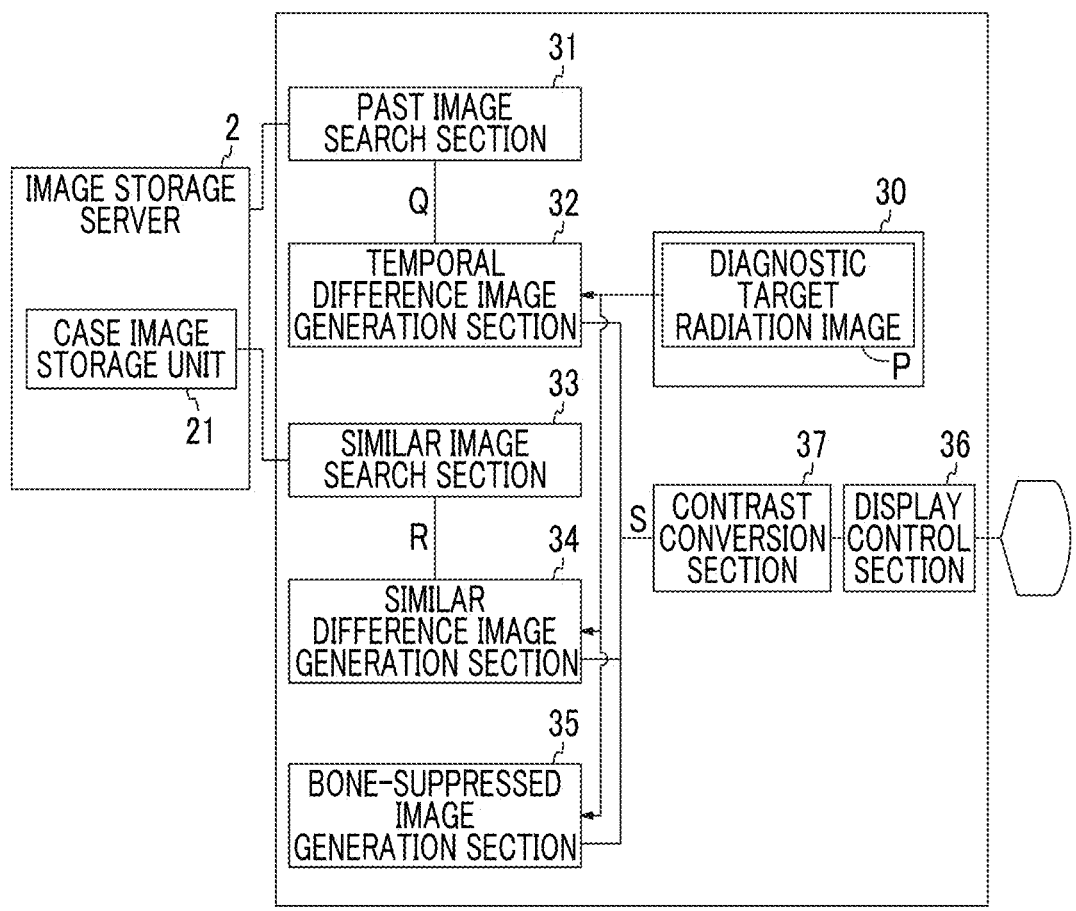

HILAR PORTION

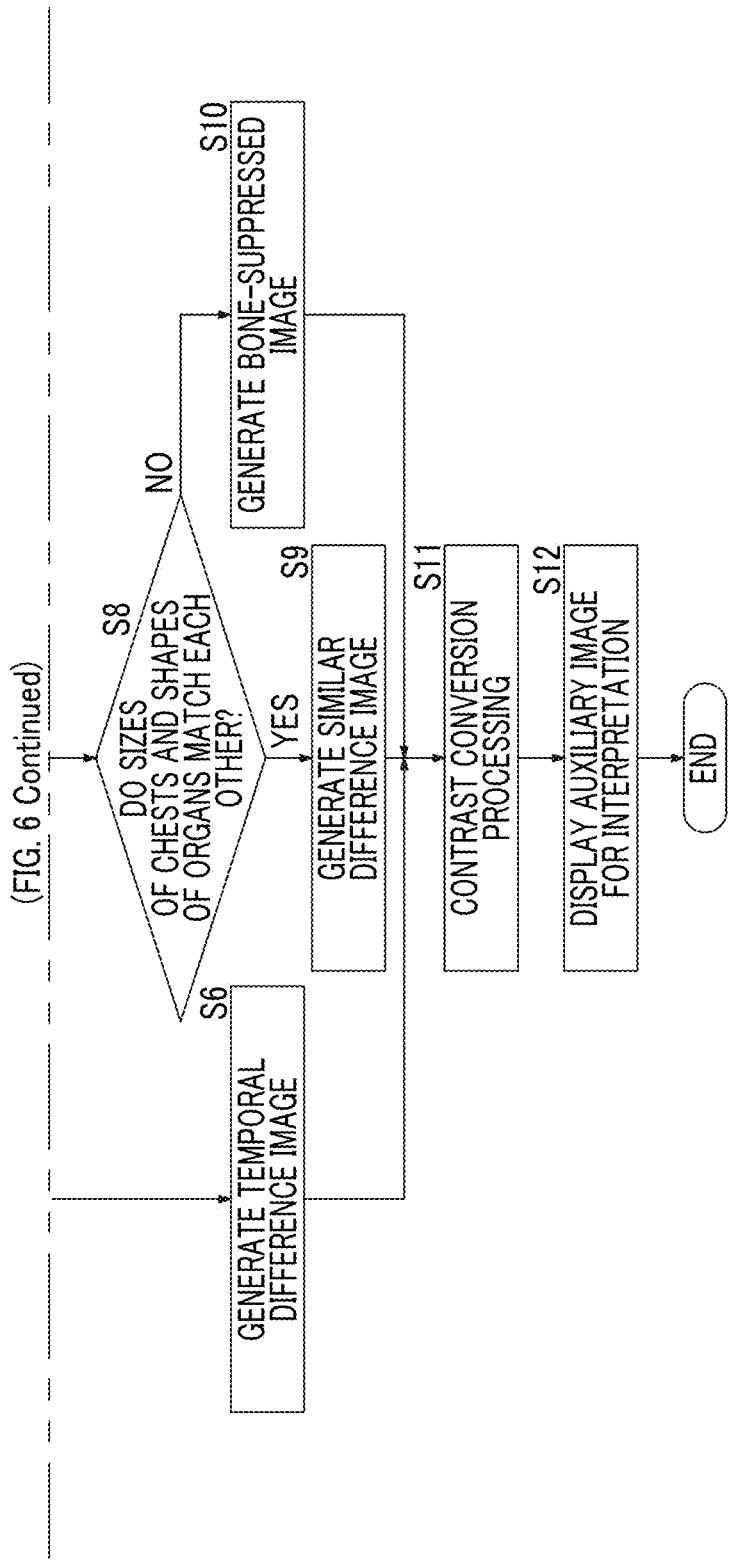

DIAGNOSTIC AUXILIARY IMAGE GENERATION APPARATUS, DIAGNOSTIC AUXILIARY IMAGE GENERATION METHOD, AND DIAGNOSTIC AUXILIARY IMAGE GENERATION PROGRAM

CROSS-REFERENCE TO RELATED APPLICATIONS

The present application claims priority under 35 U.S.C. § 119 to Japanese Patent Application No. 2015-057329, filed on Mar. 20, 2015. Each of the above application(s) is hereby expressly incorporated by reference, in its entirety, into the present application.

BACKGROUND OF THE INVENTION

1. Field of the Invention

The present invention relates to a diagnostic auxiliary image generation apparatus, a diagnostic auxiliary image generation method, and a non-transitory computer readable recording medium recorded with a diagnostic auxiliary image generation program for generating an image to assist the interpretation of a radiation image.

2. Description of the Related Art

In the case of front chest imaging that is the most common in the inspection using a radiation image, interpretation is difficult since a wide range of diseases are the target (for example, refer to Complete Medical Examination and Determination Guidelines. "Chest X-ray Screening Decision Manual" issued by Japan Society of Ningen Dock), and the front chest imaging is known as a field where computer aided detection (CAD) to assist interpretation using a computer is effective. Disease type and shade pattern correspondence is not easy even to an experienced doctor. Accordingly, an interpretation method of specifying a changed portion as a lesion through temporal comparison between a normal image obtained by imaging a patient in the past and a current image is effective.

However, an image obtained by imaging the patient in the past is not always present. Therefore, a method has been proposed in which an image of a normal example having a normal structure, which is similar to a front chest image of a certain patient, is selected from front chest images of other patients and a similar difference image is generated by subtracting the selected image from the front chest image of the patient (for example, JP2005-269214A or "Development of Computerized System for Selection of Similar Images from Different Patients for Image Subtraction of Chest Radiographs", Oda Nobuhiro et al., Biomedical Engineering Vol. 44 (2006) No. 3 pp. 435-444). In addition, when a tomographic image obtained by imaging the same patient with a CT apparatus is present, it is also possible to generate a two-dimensional chest captured image from the tomographic image (for example, JP2007-14435A).

Alternatively, attempts to see the disease easily by estimating a bone component from one image obtained by imaging the patient and removing the bone have been performed. For example, in the method disclosed in U.S. Pat. No. 7,545,965B, normal bones are learned in advance as a teacher image, bones of the input captured image are recognized, and a bone image is estimated and is subtracted from the original chest image. Therefore, since the shade of ribs overlapping the lung field is not visible, a lesion overlapping the ribs can be easily observed.

SUMMARY OF THE INVENTION

As described above, as an application to assist temporal comparison, a temporal difference image is known. In this method, however, an image captured in the past is required. In addition, if a current image of a diagnostic target and an image captured in the past are not captured in the close positioning, image subtraction occurs in a state in which the ribs, pulmonary vessels, or the like are shifted from each other. As a result, artifacts appear in the difference image, and these are obstacles to specifying a lesion.

Therefore, in order to solve the problem, a method of building a large-scale image database of only subjects determined to include no disease, searching for and selecting a case of a similar lung field shape, and obtaining a difference image (referred to as a similar difference image) using a selected image instead of a past image has been proposed in "Development of Computerized System for Selection of Similar Images from Different Patients for Image Subtraction of Chest Radiographs". Oda Nobuhiro et al., Biomedical Engineering Vol. 44 (2006) No. 3 pp. 435-444. This method is effective when there is no image captured in the past. However, there are many artifacts due to pulmonary vessels, heart, and the like having large individual differences in a difference image between an image of a diagnostic target and an image having a lung field shape similar thereto. For this reason, it has been reported that about 30% of all images are not appropriate as auxiliary images for interpretation diagnosis.

In addition, U.S. Pat. No. 7,545,965B discloses a method of estimating a bone component from one chest image in order to generate an auxiliary image for interpretation diagnosis. In this method, no past image is required, but it is difficult to accurately extract only the bone component from the chest image having a large number of shape patterns. In general, in a temporal difference image, there is an effect of increasing the interpretation efficiency by clearly visualizing a lesion by the contrast enhancement of the difference image. However, since the image obtained by subtracting the bone component is an image that is mainly configured to include soft tissues, the contrast enhancement is limited. In particular, in the case of a lung disease, a slight change in concentration may have an effect on a wide range. If the contrast of the soft tissue including the lung field is emphasized, an observation area becomes narrow. As a result, it may be difficult to understand the concentration change due to the disease.

Therefore, in order to solve the aforementioned problems, it is an object of the invention to provide a diagnostic auxiliary image generation apparatus, a diagnostic auxiliary image generation method, and a non-transitory computer readable recording medium recorded with a diagnostic auxiliary image generation program for generating an image to assist the interpretation of a radiation image that efficiently generates an optimal diagnostic auxiliary image for interpretation.

A diagnostic auxiliary image generation apparatus of the invention includes: a past image search unit that searches for a past radiation image obtained by irradiating a chest of a subject to be diagnosed, from a radiation image storage unit that stores a plurality of radiation images, before an imaging time of a diagnostic target radiation image obtained by irradiating the chest of the subject to be diagnosed; a temporal difference image generation unit that generates a temporal difference image as a diagnostic auxiliary image by performing differential processing between the diagnostic target radiation image and the past radiation image in a case where the past radiation image is found by the past image search unit and it is determined that a shape of an organ of a chest appearing on the diagnostic target radiation image matches a shape of the organ appearing on the past radiation image by comparing the shapes of the organs; a bone-suppressed image generation unit that estimates a bone component from the diagnostic target radiation image and generates a bone-suppressed image as a diagnostic auxiliary image by removing the estimated bone component from the diagnostic target radiation image in a case where the past radiation image is found by the past image search unit and it is determined that the shapes of the organs do not match each other or in a case where the past radiation image is not found by the past image search unit; and a display control unit that displays the diagnostic auxiliary image on a display device.

A diagnostic auxiliary image generation method of the invention is a diagnostic auxiliary image generation method in the diagnostic auxiliary image generation apparatus including the past image search unit, the temporal difference image generation unit, the bone-suppressed image generation unit, and the display control unit. The diagnostic auxiliary image generation method includes: a past image search step in which the past image search unit searches for the past radiation image obtained by irradiating the chest of the subject to be diagnosed, from the radiation image storage unit that stores a plurality of radiation images, before the imaging time of the diagnostic target radiation image obtained by irradiating the chest of the subject to be diagnosed; a temporal difference image generation step in which the temporal difference image generation unit generates the temporal difference image as the diagnostic auxiliary image by performing differential processing between the diagnostic target radiation image and the past radiation image in the case where the past radiation image is found by the past image search unit and it is determined that the shape of the organ of the chest appearing on the diagnostic target radiation image matches the shape of the organ appearing on the past radiation image by comparing the shapes of the organs; a bone-suppressed image generation step in which the bone-suppressed image generation unit estimates the bone component from the diagnostic target radiation image and generates the bone-suppressed image as the diagnostic auxiliary image by removing the estimated bone component from the diagnostic target radiation image in the case where the past radiation image is found by the past image search unit and it is determined that the shapes of the organs do not match each other through the comparison or in the case where the past radiation image is not found by the past image search unit; and a display step in which the display control unit displays the diagnostic auxiliary image on the display device.

A non-transitory computer readable recording medium recorded with a diagnostic auxiliary image generation program of the invention causes a computer to function as the diagnostic auxiliary image generation apparatus including: the past image search unit that searches for the past radiation image obtained by irradiating the chest of the subject to be diagnosed, from the radiation image storage unit that stores a plurality of radiation images, before the imaging time of the diagnostic target radiation image obtained by irradiating the chest of the subject to be diagnosed; the temporal difference image generation unit that generates the temporal difference image as the diagnostic auxiliary image by performing differential processing between the diagnostic target radiation image and the past radiation image in the case where the past radiation image is found by the past image search unit and it is determined that the shape of the organ of the chest appearing on the diagnostic target radiation image matches the shape of the organ appearing on the past radiation image by comparing the shapes of the organs; the bone-suppressed image generation unit that estimates the bone component from the diagnostic target radiation image and generates the bone-suppressed image as the diagnostic auxiliary image by removing the estimated bone component from the diagnostic target radiation image in the case where the past radiation image is found by the past image search unit and it is determined that the shapes of the organs do not match each other through the comparison or in the case where the past radiation image is not found by the past image search unit; and the display control unit that displays the diagnostic auxiliary image on the display device.

In addition, a diagnostic auxiliary image generation apparatus of the invention includes: a past image search unit that searches for a past radiation image obtained by irradiating a chest of a subject to be diagnosed, from a radiation image storage unit that stores a plurality of radiation images, before an imaging time of a diagnostic target radiation image obtained by irradiating the chest of the subject to be diagnosed; a case image storage unit that stores normal radiation images with no abnormalities among radiation images obtained by irradiating chests of a plurality of subjects to be compared; a temporal difference image generation unit that generates a temporal difference image as a diagnostic auxiliary image by performing differential processing between the diagnostic target radiation image and the past radiation image in a case where the past radiation image is found by the past image search unit and it is determined that a shape of an organ of a chest appearing on the diagnostic target radiation image matches a shape of the organ appearing on the past radiation image by comparing the shapes of the organs; a similar image search unit that searches for the normal radiation image, which is determined to have the same organ shape by comparing a shape of an organ of a chest appearing on the normal radiation image with a shape of the organ appearing on the diagnostic target radiation image, as a similar case image from the case image storage unit in a case where the past radiation image is found by the past image search unit and it is determined that the shapes of the organs do not match each other by the temporal difference image generation unit or in a case where the past radiation image is not found by the past image search unit; a similar difference image generation unit that generates a similar difference image as a diagnostic auxiliary image by performing differential processing between the found similar case image and the diagnostic target radiation image in a case where the similar case image is found by the similar image search unit; and a display control unit that displays the diagnostic auxiliary image on a display device.

In addition, a diagnostic auxiliary image generation method of the invention is a diagnostic auxiliary image generation method in the diagnostic auxiliary image generation apparatus including the past image search unit, the temporal difference image generation unit, the similar image search unit, the similar difference image generation unit, the display control unit, and the case image storage unit that stores normal radiation images with no abnormalities among radiation images obtained by irradiating chests of a plurality of subjects to be compared. The diagnostic auxiliary image generation method includes: a past image search step in which the past image search unit searches for the past radiation image obtained by irradiating the chest of the subject to be diagnosed, from the radiation image storage unit that stores a plurality of radiation images, before the imaging time of the diagnostic target radiation image obtained by irradiating the chest of the subject to be diagnosed; a temporal difference image generation step in which the temporal difference image generation unit generates the temporal difference image as the diagnostic auxiliary image by performing differential processing between the diagnostic target radiation image and the past radiation image in the case where the past radiation image is found by the past image search unit and it is determined that the shape of the organ of the chest appearing on the diagnostic target radiation image matches the shape of the organ appearing on the past radiation image by comparing the shapes of the organs; a similar image search step in which the similar image search unit searches for the normal radiation image, which is determined to have the same organ shape by comparing the shape of the organ of the chest appearing on the normal radiation image with the shape of the organ appearing on the diagnostic target radiation image, as the similar case image in the case where the past radiation image is found by the past image search unit and it is determined that the shapes of the organs do not match each other in the temporal difference image generation unit or in the case where the past radiation image is not found by the past image search unit; a similar difference image generation step in which the similar difference image generation unit generates the similar difference image as the diagnostic auxiliary image by performing differential processing between the found similar case image and the diagnostic target radiation image in the case where the similar case image is found by the similar image search unit; and a display step in which the display control unit displays the diagnostic auxiliary image on the display device.

In addition, a non-transitory computer readable recording medium recorded with the diagnostic auxiliary image generation program of the invention causes a computer to function as the diagnostic auxiliary image generation apparatus including: the past image search unit that searches for the past radiation image obtained by irradiating the chest of the subject to be diagnosed, from the radiation image storage unit that stores a plurality of radiation images, before the imaging time of the diagnostic target radiation image obtained by irradiating the chest of the subject to be diagnosed; the case image storage unit that stores normal radiation images with no abnormalities among radiation images obtained by irradiating chests of a plurality of subjects to be compared; the temporal difference image generation unit that generates the temporal difference image as the diagnostic auxiliary image by performing differential processing between the diagnostic target radiation image and the past radiation image in the case where the past radiation image is found by the past image search unit and it is determined that the shape of the organ of the chest appearing on the diagnostic target radiation image matches the shape of the organ appearing on the past radiation image by comparing the shapes of the organs; the similar image search unit that searches for the normal radiation image, which is determined to have the same organ shape by comparing the shape of the organ of the chest appearing on the normal radiation image with the shape of the organ appearing on the diagnostic target radiation image, as the similar case image in the case where the past radiation image is found by the past image search unit and it is determined that the shapes of the organs do not match each other by the temporal difference image generation unit or in the case where the past radiation image is not found by the past image search unit; the similar difference image generation unit that generates the similar difference image as the diagnostic auxiliary image by performing differential processing between the found similar case image and the diagnostic target radiation image in the case where the similar case image is found by the similar image search unit; and the display control unit that displays the diagnostic auxiliary image on the display device.

"Comparing the shape of the organ of the chest appearing on the diagnostic target radiation image with the shape of the organ appearing on the past radiation image" refers to comparing the same organs appearing in the diagnostic target radiation image and the past radiation image. For example, this refers to comparing the ribs between the diagnostic target radiation image and the past radiation image and comparing the lung fields between the diagnostic target radiation image and the past radiation image. Examples of the organ include ribs, heart, blood vessels, bronchi, and a lung field.

"Determining that the shapes of the organs match each other" may refer to determining that the shapes of the organs to be compared with each other approximately match each other as well as determining that the shapes of the organs completely match each other. For example, the degree of matching between the shapes of the organs overlapping each other in the images may be calculated using a method determined in advance, and it may be determined whether or not the shapes of the organs match each other according to whether or not the calculated degree of matching is greater than a threshold value or less than the threshold value. "Determining that the shapes of the organs do not match each other" refers to a case in which it is not determined that the shapes of the organs match each other.

In addition, the "subject to be diagnosed" is not included in the "subject to be compared".

The display control unit may display the diagnostic auxiliary image distinguishably displaying whether the diagnostic auxiliary image is the temporal difference image or the similar difference image or the bone-suppressed image.

For the "distinguishable display", which type of image among the temporal difference image, the similar difference image, and the bone-suppressed image the diagnostic auxiliary image is may be displayed in characters, or may be displayed using specific figures, colors, or the like matched with various types in advance. Any display may be applied as long as it is displayed on the display device so that it can be recognized which image the currently displayed diagnostic auxiliary image is.

The diagnostic auxiliary image generation apparatus of the invention may further include: a bone-suppressed image generation unit that estimates a bone component from the diagnostic target radiation image and generates a bone-suppressed image as a diagnostic auxiliary image by removing the estimated bone component from the diagnostic target radiation image in a case where the past radiation image is not found by the past image search unit and the similar case image is not found by the similar image search unit. The display control unit may display the diagnostic auxiliary image generated by the bone-suppressed image generation unit on the display device.

A contrast conversion unit that performs contrast conversion processing on the diagnostic auxiliary image may be provided, and the display control unit may display a diagnostic auxiliary image obtained after contrast conversion of the diagnostic auxiliary image by the contrast conversion unit. It is preferable that the contrast conversion unit performs different contrast conversion processing according to whether the diagnostic auxiliary image is the temporal difference image or the similar difference image or the bone-suppressed image.

It is preferable that the contrast conversion section performs contrast conversion processing for increasing all pixel values multiple times in a case where the diagnostic auxiliary image is the temporal difference image or the similar difference image and performs contrast conversion processing for emphasizing pixel values in a low frequency band lower than a specific frequency in a case where the diagnostic auxiliary image is the bone-suppressed image.

In addition, it is preferable that the specific frequency is determined in advance according to a size of a blood vessel included in the chest.

The temporal difference image generation unit may determine whether or not the shapes of the organs match each other by determining whether or not lung field shapes and/or rib shapes match each other. That is, the temporal difference image generation unit may determine whether or not the shapes of the organs match each other by determining whether or not either lung field shapes or rib shapes match each other.

Preferably, the similar image search unit includes: a first selection section that selects normal radiation images in which the subject to be compared with a subject to be diagnosed has the same sex and age range as the subject to be diagnosed; a second selection section that selects, from the normal radiation images selected by the first selection section, normal radiation images including lung field shapes that match a lung field shape of the diagnostic target radiation image; a third selection section that selects, from the normal radiation images selected by the second selection section, normal radiation images including positions of bones overlapping a lung field that matches positions of bones overlapping a lung field in the diagnostic target radiation image; and a fourth selection section that selects, from the normal radiation images selected by the third selection section, a normal radiation image including a soft structure similar to a soft structure of the diagnostic target radiation image. Preferably, the similar image search unit selects the normal radiation image having the organ shape that matches the organ shape in the diagnostic target radiation image using the first to fourth selection sections, and the similar image search unit further includes a specification section that specifies the normal radiation image selected by the fourth selection section as a similar case image.

The bone shape may be a shape of a rib or a clavicle.

The soft structure may be a shape of a heart or a pulmonary vessel.

According to the invention, in a case where a past radiation image is present, a temporal difference image is generated and set as a diagnostic auxiliary image only in a case where the shapes of the organs of the chests of the diagnostic target radiation image and the past radiation image match each other. In a case where a past image is not present or in a case where the shapes of the organs of the chests of the diagnostic target radiation image and the past radiation image do not match each other, a bone-suppressed image is generated and set as a diagnostic auxiliary image. Thus, it is possible to improve the diagnostic accuracy by generating a diagnostic auxiliary image for any diagnostic target radiation image.

BRIEF DESCRIPTION OF THE DRAWINGS

FIG. 1 is a diagram showing the schematic configuration of an interpretation diagnostic system to which a diagnostic auxiliary image generation apparatus according to a first embodiment of the invention is applied.

FIG. 2 is a functional block diagram of the diagnostic auxiliary image generation apparatus according to the first embodiment of the invention.

DESCRIPTION OF THE PREFERRED EMBODIMENTS

Figure 3:
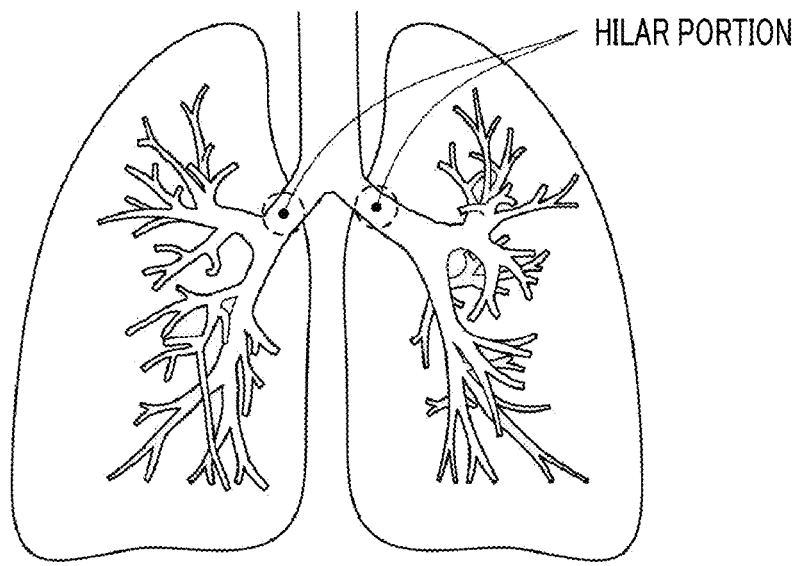
FIG. 3 is a diagram for explaining a method of calculating the similarity between pulmonary vessels.

A diagnostic auxiliary image generation apparatus according to a first embodiment of the invention will be described with reference to the accompanying diagrams.

FIG. 1 is a diagram of the hardware configuration schematically showing the interpretation diagnostic system. As shown in FIG. 1, in this system, a modality 1, an image storage server 2, and an image processing workstation 3 are communicably connected to each other through a network 4.

An apparatus that generates image data showing a diagnosis target part of a patient by imaging the part, adds supplementary information defined by the digital imaging and communications in medicine (DICOM) standards to the image data, and outputs the result as image information is included in the modality 1. Specifically, the modality 1 will be described below as a simple X-ray imaging apparatus, for example.

The image storage server (radiation image storage unit) 2 is a computer that stores image data acquired in various modalities in an image database and manages the image data, and includes a large-capacity external storage device or database management software (for example, object relational database (ORDB) management software). Image data that is present in each medical institution and is obtained by imaging a number of patients in various modalities is stored in the image storage server 2. In the present embodiment, a case will be described in which the modality is a simple X-ray imaging apparatus and the image data is a simple X-ray image.

The image processing workstation 3 is a computer that performs image processing on the image data obtained from the modality 1 or the image storage server 2 in response to a request from the user, and has a known hardware configuration including a central processing unit (CPU), a main storage device, an auxiliary storage device, an input and output interface, a communication interface, an input device (a mouse, a keyboard, and the like), a display device (display monitor), and a data bus. A known operating system or the like is installed in the image processing workstation 3. Diagnostic auxiliary image generation processing of the invention is performed by the image processing workstation 3, and this processing is realized by executing an installed program from the recording medium, such as a CD-ROM. In addition, the program may be installed after being downloaded from the storage device of a server connected through a network, such as the Internet.

FIG. 2 is a block diagram showing a diagnostic auxiliary image generation processing unit in the first embodiment of the invention among the functions of the image processing workstation 3. As shown in FIG. 2, the diagnostic auxiliary image generation processing unit in the first embodiment of the invention includes a diagnostic target image storage section 30, a past image search section 31, a temporal difference image generation section 32, a similar image search section 33, a similar difference image generation section 34, a bone-suppressed image generation section 35, a display control section 36, and a contrast conversion section 37. A case image storage unit 21 is provided in the image storage server 2, and the diagnostic auxiliary image generation processing unit of the image processing workstation 3 and the case image storage unit 21 function as an auxiliary image generation apparatus of the invention.

A diagnostic target radiation image P of a subject to be diagnosed is stored in the diagnostic target image storage section 30.

The past image search section 31 searches for a past radiation image Q, which has been obtained by imaging a subject (patient) to be diagnosed with a simple X-ray imaging apparatus, from the image storage server 2 before the imaging time of a diagnostic target radiation image at which the same subject has been imaged by the modality 1. Specifically, the past image search section 31 searches for a radiation image, which has the same patient ID and the same imaging part and has been captured before the imaging time of the diagnostic target radiation image P, based on the supplementary information defined by the DICOM standards. Hereinafter, a case in which a diagnostic target part is a chest will be described.

When imaging the chest of a subject to be diagnosed, the subject is irradiated for the imaging. However, depending on a direction in which the subject is irradiated, that is, depending on a projection direction in which the chest is projected, the shape of the lung field appearing on the radiation image, the shape of the ribs or clavicles appearing on the radiation image, or the traveling direction of the blood vessels of a soft portion appearing on the radiation image is different. Even if the same subject is imaged, the projection direction when capturing the diagnostic target radiation image P is different from the projection direction when the past radiation image Q was captured, in many cases, depending on the standing position of the subject with respect to the modality 1 and/or the posture of the subject. When the projection directions are greatly different, the shape of the lung field of the chest appearing on the radiation image, the shape of the ribs or clavicles appearing on the radiation image, or the traveling direction of the blood vessels of a soft portion appearing on the radiation image is different. In addition, when the breathing state at the time of imaging is different, the shape of the lung field is different. The difference between the projected images of the organ appearing on the radiation images appears as an artifact when generating a difference image.

Therefore, the temporal difference image generation section 32 compares the shape of the organ of the past radiation image Q, which has been found by the past image search section 31, with the shape of the organ of the projected image appearing on the diagnostic target radiation image P to determine whether or not the two projected images match each other. Specifically, in order to determine whether or not the lung field shapes and/or the rib shapes of projected images appearing on the past radiation image Q and the diagnostic target radiation image P, the temporal difference image generation section 32 calculates the degree of matching between the lung field shapes and/or the rib shapes. Then, when the degree of matching is equal to or greater than a predetermined threshold value, the temporal difference image generation section 32 determines that the lung field shapes and/or the rib shapes match each other.

For example, in order to calculate the degree of matching between the lung field shapes, a lung field region is first detected from the diagnostic target radiation image P and the past radiation image Q. For the extraction of a lung field region, a binary image for a radiation image obtained by imaging the chest is generated by performing binarization with a predetermined threshold value as a boundary, a region in contact with the image end is set as a region other than the lung field by performing labeling on the generated binary image, and a region that is not in contact with the image end is extracted as a lung field region (for the details of the extraction of the lung field region, refer to JP1999-151232A (JP-H11-151232A) and the like). For example, it is possible to superimpose lung field regions of the diagnostic target radiation image P and the past radiation image Q and determine the degree of matching from the ratio of the area of a product set region of the lung field regions to a sum set region of the lung field regions. Alternatively, the degree of matching between the lung field shapes may be obtained by detecting the lung field contour in each image using the density pattern characteristic of pixels (for the details of the detection of the lung field contour, refer to JP1988-240832A (JP-S63-240832A) and the like).

Since the difference between the lung field shapes can be determined even in quite small images, it is possible to reduce the determination cost by using the reduced images of the diagnostic target radiation image P and the past radiation image Q when extracting the lung field shapes. The degree of reduction may be determined according to the determination accuracy to be required.

In addition, the degree of matching between the rib shapes is calculated by extracting rib regions from the diagnostic target radiation image P and the past radiation image Q. For example, a rib region is extracted from the edge of the contour of the ribs appearing in the lung field in a radiation image and the pattern of the pixel value of the radiation having passed through the ribs (for details, refer to US2013/0108135A1 and the like). Similar to the degree of matching between the lung field shapes, the degree of matching between the ribs can be determined from the area ratio of a product set region of the rib regions to a sum set region of the rib regions.

In order to determine whether or not the shapes of the organs of the diagnostic target radiation image P and the past radiation image Q match each other, a method of determining whether or not the shapes of the organs match each other by extracting the lung field shapes to determine whether or not the lung field shapes match each other and then determining that the shapes of the organs do not match each other without determining the matching between the rib shapes when the lung field shapes do not match each other and further determining whether or not the rib shapes match each other when the lung field shapes match each other may be used since the accuracy is high if the degree of matching between the rib shapes is determined but the high calculation cost is required for the extraction of the rib shapes. If there is no problem in calculation cost, determination using only the rib shapes is also possible.

As described above, the temporal difference image generation section 32 determines whether or not the projected images of the diagnostic target radiation image P and the past radiation image Q match each other from the degree of matching between the lung field shapes and the degree of matching between the rib shapes. When it is determined that the projected image of the chest appearing on the diagnostic target radiation image P approximately matches the projected image of the chest appearing on the past radiation image Q, the temporal difference image generation section 32 generates a temporal difference image between the past radiation image Q and the diagnostic target radiation image P as a diagnostic auxiliary image S. On the other hand, when the projected image of the past radiation image Q and the diagnostic target radiation image P do not match each other, a temporal difference image is not generated.

Normal radiation images, which are obtained by imaging the chests of a number of subjects (subjects to be compared) and in which no abnormal shade appears, are stored in the case image storage unit 21. Normal radiation images may be selected from the radiation images stored in the image storage server 2. The stored normal radiation images are radiation images obtained by imaging only subjects for which it is determined that there is no disease in the chests of the imaged subjects. It is preferable to store normal radiation images that are captured over the wide range of age groups so that images, which are obtained by imaging the lung fields of various sizes, are included. Supplementary information defined by the DICOM standards is added to the normal radiation image, and the sex and age of each subject, imaged modalities, imaging conditions, and the like are included in the supplementary information.

When it is determined that the projected images of the diagnostic target radiation image P and the past radiation image Q do not match each other even if the past radiation image Q of the patient to be diagnosed is found by the past image search section 31 or when the past radiation image Q is not found by the past image search section 31, the similar image search section 33 compares the size of the chest of each normal radiation image with the size of the chest of the diagnostic target radiation image P and compares the shape of the organ projected on each normal radiation image with the shape of the organ of the diagnostic target radiation image P, searches for a normal radiation image, which is determined to be almost the same by this comparison, from the case image storage unit 21, and sets the normal radiation image as a similar case image R.

Figure 5:
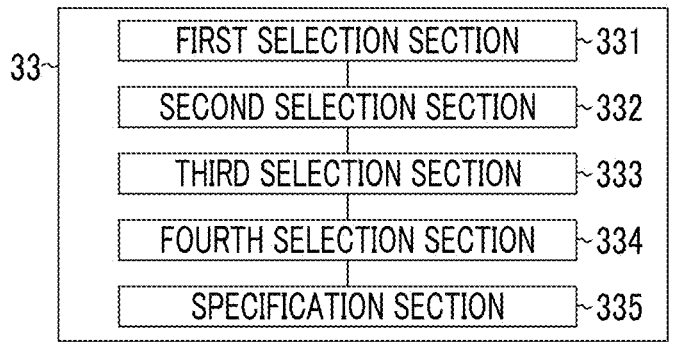
FIG. 5 is a detailed functional block diagram of a similar image search section.

As shown in FIG. 5, the similar image search section 33 includes a first selection section 331, a second selection section 332, a third selection section 333, a fourth selection section 334, and a specification section 335. In order to determine whether or not the sizes of the chests and the shapes of the organs are similar, the specification section 335 specifies a normal radiation image, which is the most similar to the diagnostic target radiation image P, as the similar case image R after selecting normal radiation images by the first selection section 331, the second selection section 332, the third selection section 333, and the fourth selection section 334.

First, the first selection section 331 selects a normal radiation image, in which a subject to be compared with a subject to be diagnosed has the same sex and age range as the subject to be diagnosed, based on the supplementary information. For example, in the case of a woman, a breast is reflected in the radiation image. That is, the way in which a breast is reflected differs depending on the sex, and the rib shape also differs depending on the sex. Therefore, a normal radiation image is selected from the matching of sex. In addition, the size of the rib cage significantly changes until the adult in accordance with the growth, and the shape or size of the lung or ribs changes greatly depending on the age range (any of neonates, infants, young children, children, and adults). Then, a normal radiation image is selected from the same age range.

Then, the second selection section 332 selects, from the normal radiation images selected by the first selection section 331, a normal radiation image including a lung field shape that matches the lung field shape appearing in the diagnostic target radiation image P. For the determination of the similarity between the lung field shapes, it is possible to use the above method described when comparing the projected images using the temporal difference image generation section 32.

Then, the third selection section 333 selects, from the normal radiation images selected by the second selection section 332, a normal radiation image having a positional relationship between the lung field and the bones overlapping the lung field that is similar to that in the diagnostic target radiation image P. In particular, since there are individual differences in the positional relationship between the lung and the bones, such as the ribs and/or clavicles overlapping the lung, a normal radiation image having a similar positional relationship is left as a candidate. For the determination of the similarity between the rib shapes or between the clavicle shapes, the degree of matching is calculated according to how much of the information of a high frequency band, which is higher than a predetermined band considered to include image components of the bone, match each other, and an image having a high degree of matching is selected. Specifically, an image of high frequency components higher than a predetermined band is generated, and the degree of matching is determined using any of the average of pixel value differences, cross-correlation, mutual information, and the like. Alternatively, it is also possible to use the method of extracting the shape of the bone that has been described when comparing the projected images using the temporal difference image generation section 32 for the determination of the similarity between the rib shapes or between the clavicle shapes.

Finally, the fourth selection section 334 selects, from the normal radiation images selected by the third selection section 333, a normal radiation image including a soft structure similar to the soft structure appearing in the diagnostic target radiation image P. In particular, since there are individual differences in the positional relationship between the lung and the heart and the pulmonary vessels that are soft structures, a normal radiation image having a similar positional relationship is left as a candidate. The pulmonary vessels are extracted from the blood vessel likeness pixel value, but the individual difference is very large in the shape of the pulmonary vessels. Since the blood vessels are divided along the bronchus from the hilar portion, the similarity is calculated with an emphasis on the hilar portion. For example, as shown in FIG. 3, the position of the hilar portion is detected first, and the weight in the calculation of the degree of matching is reduced as the position moves from the hilar portion to the peripheral part of the bronchus. Alternatively, the degree of matching between the shapes of recognized organs, such as the heart, is determined by measuring the similarity of the pixel values using any of the average of pixel value differences, cross-correlation, mutual information, and the like and comparing the similarity with a threshold value.

The specification section 335 specifies a normal radiation image narrowed down by the four selection sections described above most similar to the diagnostic target radiation image P, as the similar case image R.

When the similar case image R is found by the similar image search section 33, the similar difference image generation section 34 generates a similar difference image as the diagnostic auxiliary image S by performing differential processing between the found similar case image R and the diagnostic target radiation image P.

Figure 4:
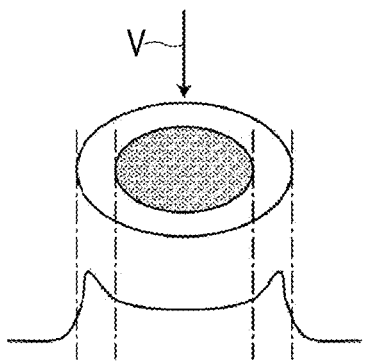
FIG. 4 is a diagram for explaining the tissue of the bone and the profile of the concentration appearing in the shape of a radiation image.

When the past radiation image Q is not found by the past image search section 31 and the similar case image R is not found by the similar image search section 33, the bone-suppressed image generation section 35 estimates bone components from the diagnostic target radiation image P and generates a bone-suppressed image as the diagnostic auxiliary image S by removing the estimated bone components from the diagnostic target radiation image P. For the estimation of bone components, a feature quantity obtained by quantifying the characteristics of the bone is learned in advance using the bone of a normal example as a teacher image. Then, based on the bone likeness for each pixel in the diagnostic target radiation image P, the pixel value of the bone component for each pixel is estimated. A bone appears as a low-concentration portion since the X-ray absorption is large compared with the surrounding tissue, and the imaging portion of the bone appears as a region surrounded by the edge structure. As shown in the upper portion of FIG. 4, a boundary portion of the bone with respect to the surrounding tissue is covered with a cortical bone (white portion), and is drawn with a low concentration. In addition, the center of the bone has a higher concentration than the cortical bone since a portion in which the X-ray absorption is slightly small, such as bone marrow (hatched portion), is present. For example, when the bone is irradiated with X-rays from the direction of V, a profile of a pixel value that is determined to some extent according to the part of the bone is obtained, as shown in a lower portion of FIG. 4. A bone-suppressed image in which bone components are suppressed can be generated by subtracting the estimated bone components from the inspection image according to the feature of the profile (for example, refer to US2013/0108135A1 and the like). This bone-suppressed image is set as the diagnostic auxiliary image S.

The abnormal shade appearing in the chest radiation image is light shade in many cases. In addition, since the difference between the shade, which appears in a temporal difference image, a similar difference image, or a bone-suppressed image, and the surrounding image is small, the shade cannot be understood well in many cases.

Therefore, the contrast conversion section 37 performs contrast conversion processing on the diagnostic auxiliary image S. In the temporal difference image or the similar difference image, not only bones but also blood vessels and organs, such as the lung and the heart, disappear by the difference, and only a portion where there has been a change, such as a tumor, remains. However, in the bone-suppressed image, blood vessels and organs, such as the lung and the heart, other than bones remain without disappearing. Therefore, the contrast conversion section 37 performs different contrast conversion processing according to whether the diagnostic auxiliary image S is a temporal difference image or a similar difference image or a bone-suppressed image.

Specifically, when the diagnostic auxiliary image S is a temporal difference image or a similar difference image, the contrast conversion section 37 performs contrast conversion processing for emphasis by increasing all the pixel values multiple times (for example, two or three times), for example. When the diagnostic auxiliary image S is a bone-suppressed image, the contrast conversion section 37 performs contrast conversion processing for emphasizing the pixel values in a low frequency band lower than a specific frequency. In the temporal difference image, bones, blood vessels, and organs, such as the lung and the heart, disappear. Accordingly, it is possible to emphasize the light shade just by enlarging all images two or three times. On the other hand, when the diagnostic auxiliary image S is a bone-suppressed image, bones disappear, but blood vessels remain. Blood vessels are scattered in the lung field, and blood vessels other than blood vessels near the hilar portion appear as the thin and light shade. In order to suppress the shade of the blood vessels, contrast conversion processing for emphasizing the pixel values of the low frequency band lower than a specific frequency is performed. The specific frequency is determined so that the shade, which is round and has a certain size (for example, 1 cm or more) like a tumor, can be emphasized without emphasizing the thin and light shade appearing in a place slightly away from the hilar portion.

The display control section 36 displays the diagnostic auxiliary image S on a display device. When displaying the diagnostic auxiliary image S on the display device, whether the diagnostic auxiliary image S is a temporal difference image or a similar difference image or a bone-suppressed image is displayed near the diagnostic auxiliary image S (refer to FIG. 7). The diagnostic auxiliary image S is used to assist the diagnosis, and the final diagnosis is performed by interpreting the original diagnostic target radiation image P. Understanding what kind of image the diagnostic auxiliary image S is becomes important in performing interpretation. Whether the diagnostic auxiliary image S is a temporal difference image or a similar difference image or a bone-suppressed image may be displayed so as to be distinguishable, or a specific mark may be displayed. Although the diagnostic auxiliary image S may be displayed on the display device as it is, it is desirable to display the processed diagnostic auxiliary image S after contrast conversion by the contrast conversion section 37 on the display device.

Next, the operation of the diagnostic auxiliary image generation apparatus according to the first embodiment will be described with reference to the flowchart of FIG. 6.

The chest of the subject to be diagnosed is imaged using a simple X-ray imaging apparatus 1. Supplementary information according to the DICOM standards is added to the captured diagnostic target radiation image P, and the result is transmitted to the image processing workstation 3. The image processing workstation 3 stores the received diagnostic target radiation image P in the diagnostic target image storage section 30 (S1).

The past image search section 31 searches for the past radiation image Q of the same patient ID as the diagnostic target radiation image P, which has been captured in the past, from the image storage server 2 (S2).

When the past radiation image Q is found (S3 YES), the temporal difference image generation section 32 compares the shape of the organ of the chest appearing on the diagnostic target radiation image P with the shape of the organ appearing on the past radiation image Q (S4). When it is determined that the shape of the organ of the chest appearing on the diagnostic target radiation image P matches the shape of the organ appearing on the past radiation image Q (S5 YES), the temporal difference image generation section 32 generates a temporal difference image by performing differential processing between the diagnostic target radiation image P and the past radiation image Q, and sets the temporal difference image as a diagnostic auxiliary image (S6).

When the past radiation image Q is not found (S3 NO) or when it is determined that the shape of the organ in the diagnostic target radiation image P does not match the shape of the organ in the past radiation image Q even if the past radiation image Q is found (S5 NO), the size of the chest and the shape of the organ in the diagnostic target radiation image P are compared with the size of the chest and the shape of the organ in a normal radiation image (S7). From the normal radiation images stored in the case image storage unit 21 that are determined to almost match the diagnostic target radiation image P by this comparison, an image that best matches the diagnostic target radiation image P is searched for as the similar case image R. When the similar case image R is found (S8 YES), a similar difference image is generated by performing differential processing between the diagnostic target radiation image P and the similar case image R (S9), and the similar difference image is set as the diagnostic auxiliary image S (S9).

When the past radiation image Q is not found (S3 NO) and the similar case image R suitable for generating a difference image is not found from the normal radiation images (S8 NO), a bone-suppressed image is generated from the diagnostic target radiation image P (S10), and the bone-suppressed image is set as the diagnostic auxiliary image S.

Figure 7:
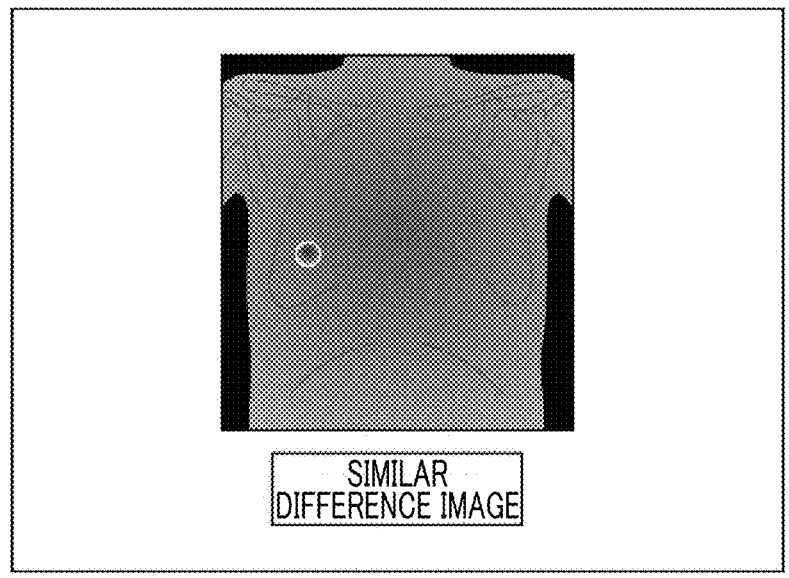
FIG. 7 is an example in which a diagnostic auxiliary image is displayed together with its kind.

Then, according to whether the generated diagnostic auxiliary image is a temporal difference image or a similar difference image or a bone-suppressed image, contrast conversion processing is performed by the contrast conversion section 37 (S11). A diagnostic auxiliary image after the contrast conversion processing is displayed on the display device by the display control section 36 (S12). When displaying the diagnostic auxiliary image, as shown in FIG. 7, whether the diagnostic auxiliary image S is a temporal difference image or a similar difference image or a bone-suppressed image is displayed below the diagnostic auxiliary image S.

As described above, when a past radiation image is present, a temporal difference image is generated and set as a diagnostic auxiliary image only when the projected images of the diagnostic target radiation image and the past radiation image almost match each other. When a past image is not present or when the projected images of the diagnostic target radiation image and the past radiation image do not match each other even if a past radiation image is present, a similar case image is searched for to generate a similar difference image, and the similar difference image is set as a diagnostic auxiliary image. When the similar difference image is not present either, a bone-suppressed image is generated and set as a diagnostic auxiliary image. Thus, it is possible to improve the diagnostic accuracy by generating a diagnostic auxiliary image for any diagnostic target radiation image.

Next, a diagnostic auxiliary image generation apparatus according to a second embodiment will be described. In the second embodiment, a case will be described in which a similar difference image is not generated. The same components as in the first embodiment are denoted by the same reference numerals, and the detailed explanation thereof will be omitted.

Figure 8:
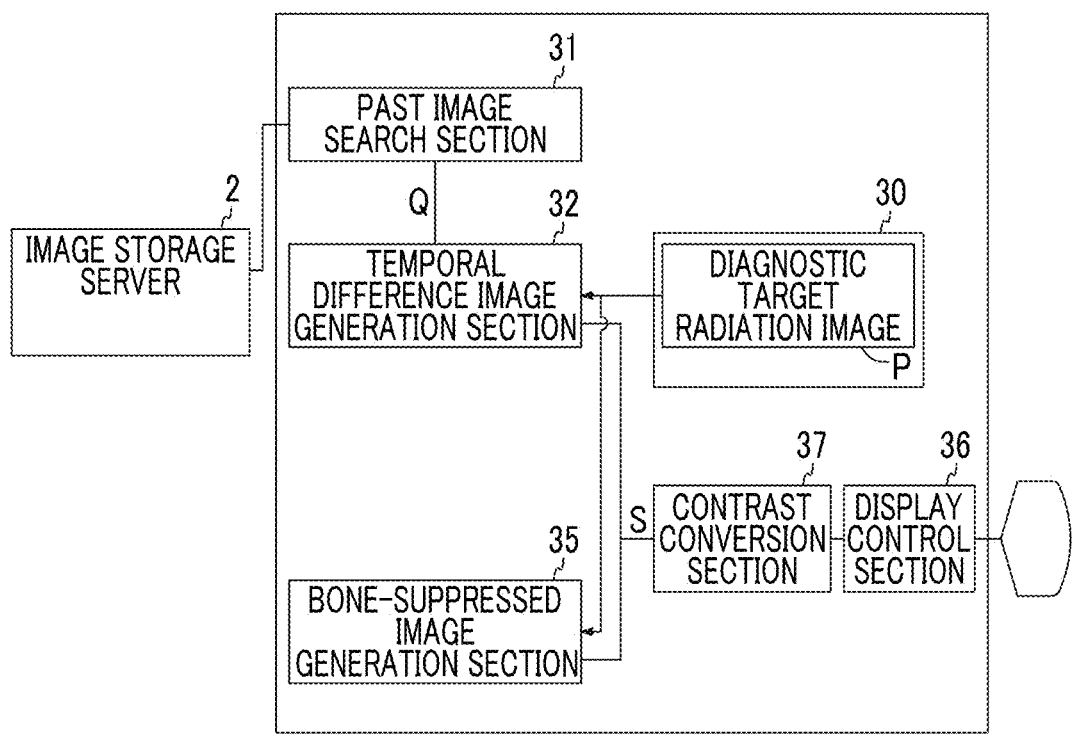
FIG. 8 is a functional block diagram showing a diagnostic auxiliary image generation processing unit in a second embodiment of the invention.

FIG. 8 is a block diagram showing a diagnostic auxiliary image generation processing unit in the second embodiment. As shown in FIG. 8, the diagnostic auxiliary image generation processing unit in the embodiment of the invention includes a diagnostic target image storage section 30, a past image search section 31, a temporal difference image generation section 32, a bone-suppressed image generation section 35, a display control section 36, and a contrast conversion section 37.

Figure 9:
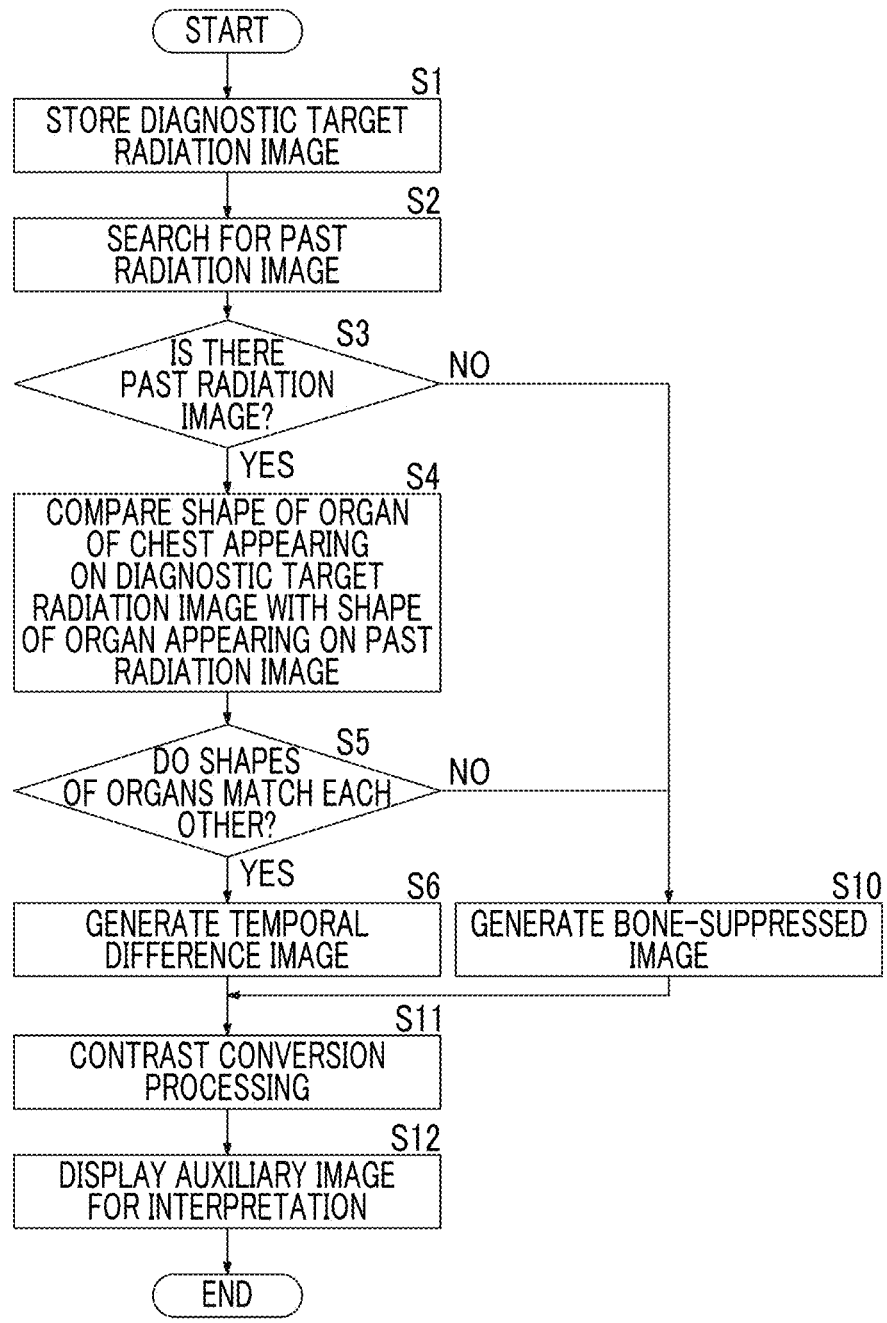
FIG. 9 is a flowchart illustrating the operation of a diagnostic auxiliary image generation apparatus according to the second embodiment of the invention.

Next, the operation of the diagnostic auxiliary image generation apparatus according to the second embodiment will be described with reference to the flowchart of FIG. 9.

The chest of the subject to be diagnosed is imaged using a simple X-ray imaging apparatus 1. Supplementary information is added to the captured diagnostic target radiation image P, and the result is transmitted to the image processing workstation 3. The image processing workstation 3 stores the received diagnostic target radiation image P in the diagnostic target image storage section 30 (S1).

The past image search section 31 searches for the past radiation image Q of the same patient ID as the diagnostic target radiation image P, which has been captured in the past, from the image storage server 2 (S2).

When the past radiation image Q is found (S3 YES), the temporal difference image generation section 32 compares the shape of the organ of the chest appearing on the diagnostic target radiation image P with the shape of the organ appearing on the past radiation image Q (S4). Only when it is determined that the shape of the organ of the chest appearing on the diagnostic target radiation image P matches the shape of the organ appearing on the past radiation image Q (S5 YES), the temporal difference image generation section 32 generates a temporal difference image by performing differential processing between the diagnostic target radiation image P and the past radiation image Q, and sets the temporal difference image as a diagnostic auxiliary image (S6).

When the past radiation image Q is not found (S3 NO) or when it is determined that the shapes of the organs do not match each other even if the past radiation image Q is found (S5 NO), a bone-suppressed image is generated from the diagnostic target radiation image P (S10), and is set as the diagnostic auxiliary image S.

Then, according to whether the generated diagnostic auxiliary image is a temporal difference image or a bone-suppressed image, contrast conversion processing is performed by the contrast conversion section 37 (S11). A diagnostic auxiliary image after the contrast conversion processing is displayed on the display device by the display control section 36 (S12). When displaying the diagnostic auxiliary image, as shown in FIG. 7, whether the diagnostic auxiliary image S is a temporal difference image or a bone-suppressed image is displayed next to the diagnostic auxiliary image S.

In order to generate a similar difference image as in the first embodiment, it is necessary to prepare the case image storage unit 21 that stores normal radiation images which are obtained by imaging the chests of a number of subjects and in which no abnormal shade appears. However, it is necessary to store a large number of normal radiation images in order to correspond to many types of subjects. When a past radiation image cannot be found, a bone-suppressed image may be generated from the diagnostic target radiation image. In this case, since a diagnostic auxiliary image is generated without preparing the case image storage unit 21, it is possible to improve the diagnostic accuracy.

Next, a diagnostic auxiliary image generation apparatus according to a third embodiment will be described. In the third embodiment, a case will be described in which a bone-suppressed image is not generated. The same components as in the first and second embodiments are denoted by the same reference numerals, and the detailed explanation thereof will be omitted.

Figure 10:
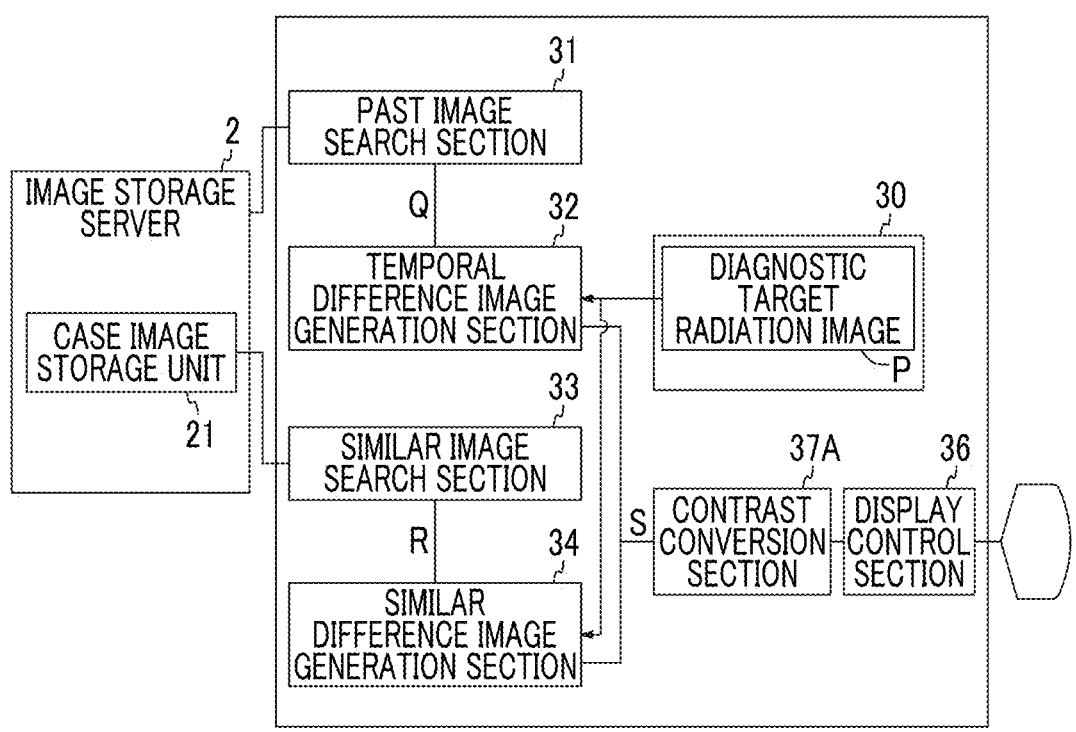
FIG. 10 is a functional block diagram showing a diagnostic auxiliary image generation processing unit in a third embodiment.

FIG. 10 is a block diagram showing a diagnostic auxiliary image generation processing unit in the third embodiment. As shown in FIG. 10, the diagnostic auxiliary image generation processing unit in the embodiment of the invention includes a diagnostic target image storage section 30, a past image search section 31, a temporal difference image generation section 32, a similar image search section 33, a similar difference image generation section 34, a display control section 36, and a contrast conversion section 37A. A case image storage unit 21 is provided in the image storage server 2, and the diagnostic auxiliary image generation processing unit of the image processing workstation 3 and the case image storage unit 21 function as an auxiliary image generation apparatus of the invention.

Figure 6:
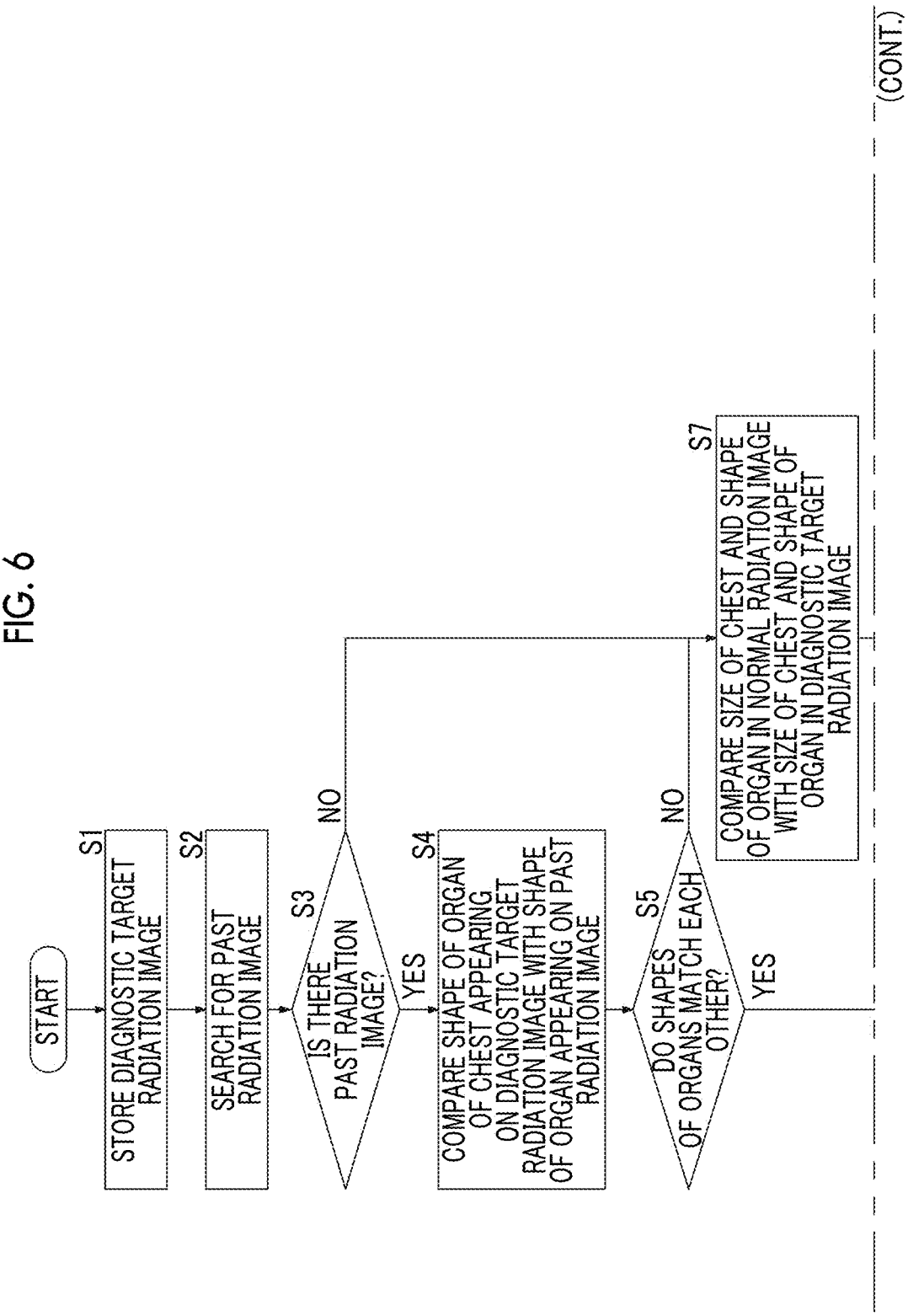
FIG. 6 is a flowchart illustrating the operation of the diagnostic auxiliary image generation apparatus according to the first embodiment.

Although the operation flow of the diagnostic auxiliary image generation apparatus according to the third embodiment is almost the same as the operation flow in the first embodiment, step S10 in the flowchart of FIG. 6 is not performed. In addition, since the diagnostic auxiliary image S is only a temporal difference image or a similar difference image, the contrast conversion section 37A performs only processing for converting the contrast by increasing all the pixel values two or three times.

When the case image storage unit 21 that stores normal radiation images, which are obtained by imaging the chests of a number of subjects and in which no abnormal shade appears, is prepared, a similar difference image is generated and set as a diagnostic auxiliary image even if a past radiation image cannot be found. Therefore, it is possible to improve the diagnostic accuracy.

The invention is not limited to the present embodiment, and some or all of the components of the diagnostic auxiliary image generation apparatus may be formed by one computer, or may be formed by one or more computers, servers, and storage devices that are connected to each other through a network.

What is claimed is:

1. A diagnostic auxiliary image generation apparatus, comprising:
  an image storage unit configured to store a plurality of radiation images, and
  a processor configured to
  search for a past radiation image, including past organ shape information, obtained by irradiating a chest of a subject to be diagnosed, from the plurality of radiation images, before an imaging time of a diagnostic target radiation image obtained by irradiating the chest of the subject to be diagnosed;
  determine whether the search locates the past radiation image;
  acquire organ shape information from the diagnostic target radiation image;
  wherein when it is determined that the search locates the past radiation image further comparing the shape of the acquired organ shape information of the diagnostic target radiation image with the organ shape information of the past radiation image, and wherein when the shape of the acquired organ shape information matches with the organ shape information of the past radiation image, said processor generates a temporal difference image as a diagnostic auxiliary image by performing differential processing between the diagnostic target radiation image and the past radiation image, and
  wherein when it is determined that the search does not locate the past radiation information or when the shape of the acquired organ shape information does not match the organ shape information of the past radiation image, said processor estimates a bone component from the diagnostic target radiation image and generates a bone-suppressed image as a diagnostic auxiliary image by removing the estimated bone component from the diagnostic target radiation image, and
  said processor further displays the diagnostic auxiliary image on a display device,
  wherein the temporal difference image that is generated between the past radiation image and the diagnostic target radiation image, satisfies at least:
  a degree of matching from a ratio of an area of a product set region of lung field regions to a sum set region of the lung field regions by using superimposed lung field regions of the diagnostic target radiation image and the past radiation image is equal to or greater than a predetermined threshold value, or the degree of matching from the ratio of the area of a product set region of rib regions to a sum set region of the rib regions by using superimposed rib regions of the diagnostic target radiation image and the past radiation image is equal to or greater than a predetermined threshold value,
  wherein the bone-suppressed image by removing the estimated bone components from the diagnostic target radiation image, and the estimated bone components is specified estimated the pixel value of the bone component for each pixel, based on a bone likeness for each pixel in the diagnostic target radiation image, by using a feature quantity obtained by quantifying characteristics of the bone is learned in advance using the bone of a normal example as a teacher image.

2. The diagnostic auxiliary image generation apparatus according to claim 1,
  wherein the processor is configured to display the diagnostic auxiliary image distinguishably displaying whether the displayed diagnostic auxiliary image is the temporal difference image or the bone-suppressed image.

3. The diagnostic auxiliary image generation apparatus according to claim 1,
  wherein the processor is configured to
  perform contrast conversion processing on the diagnostic auxiliary image,
  display a diagnostic auxiliary image obtained after contrast conversion of the diagnostic auxiliary image, and
  perform different contrast conversion processing according to whether the diagnostic auxiliary image is the temporal difference image or the bone-suppressed image.

4. The diagnostic auxiliary image generation apparatus according to claim 2,
  wherein the processor is configured to
  perform contrast conversion processing on the diagnostic auxiliary image,
  display a diagnostic auxiliary image obtained after contrast conversion of the diagnostic auxiliary image, and
  perform different contrast conversion processing according to whether the diagnostic auxiliary image is the temporal difference image or the bone-suppressed image.

5. A diagnostic auxiliary image generation apparatus, comprising:
- an image storage unit configured to store a plurality of radiation images, and
- a processor configured to
- search for a past radiation image including organ shape information, which is obtained by irradiating a chest of a subject to be diagnosed, from the plurality of radiation images, before an imaging time of a diagnostic target radiation image obtained by irradiating the chest of the subject to be diagnosed,
- store normal radiation images to the image storage unit with no abnormalities among radiation images obtained by irradiating chests of a plurality of subjects to be compared,
- determine whether the search locates the past radiation image;
- acquire organ shape information from the diagnostic target radiation image;
- wherein when it is determined that the search locates the past radiation image, further comparing the shape of the acquired organ shape information of the diagnostic target radiation image with the organ shape information of the past radiation image, and wherein when the shape of the acquired organ shape information matches with the organ shape information of the past radiation image, said processor generates a temporal difference image as a diagnostic auxiliary image by performing differential processing between the diagnostic target radiation image and the past radiation image, and
- wherein when it is determined that the search does not locate the past radiation information or when the shape of the acquired organ shape information does not match the organ shape information of the past radiation image, said processor searches for the normal radiation image, which is determined to have a same organ shape by comparing a shape of an organ of a chest appearing on the normal radiation image with a shape of the organ appearing on the diagnostic target radiation image, as a found similar case image, and
- generates a similar difference image as a diagnostic auxiliary image by performing differential processing between the found similar case image and the diagnostic target radiation image; and
  - wherein in a case where it is determined that the search does not locate the past radiation information and in a case where the shape of the acquired organ shape information does not match the organ shape information of the similar case image, said processor estimates a bone component from the diagnostic target radiation image and generates a bone-suppressed image as a diagnostic auxiliary image by removing the estimated bone component from the diagnostic target radiation image, and
- said processor displays the diagnostic auxiliary image on a display device,
- wherein the temporal difference image that is generated between the past radiation image and the diagnostic target radiation image, satisfies at least:
- a degree of matching from a ratio of an area of a product set region of lung field regions to a sum set region of the lung field regions by using superimposed lung field regions of the diagnostic target radiation image and the past radiation image is equal to or greater than a predetermined threshold value, or the degree of matching from the ratio of the area of a product set region of rib regions to a sum set region of the rib regions by using superimposed rib regions of the diagnostic target radiation image and the past radiation image is equal to or greater than a predetermined threshold value,
- wherein the similar difference image is specified by performing differential processing between the found similar case image and the diagnostic target radiation image, and the similar case image is a normal radiation image most similar to the diagnostic target radiation image specified from the following conditions among the stored normal radiation images:
- (I) having the same sex and age range as the diagnostic target radiation image;
- (II) the degree of matching from the ratio of the area of a product set region of the lung field regions to a sum set region of the lung field regions by using superimposed lung field regions of the diagnostic target radiation image and the past radiation image and the degree of matching from the ratio of the area of a product set region of the rib regions to a sum set region of the rib regions by using superimposed rib regions of the diagnostic target radiation image and the past radiation image;
- (III) having a positional relationship between the lung field and the bones overlapping the lung field that is similar to that in the diagnostic target radiation image;
- (IV) having a positional relationship between the lung field and the bones overlapping the lung field that is similar to that in the diagnostic target radiation image including a soft structure similar to the soft structure appearing in the diagnostic target radiation image,
- wherein the bone-suppressed image by removing the estimated bone components from the diagnostic target radiation image, and the estimated bone components is specified estimated the pixel value of a bone component for each pixel, based on bone likeness for each pixel in the diagnostic target radiation image, by using a feature quantity obtained by quantifying characteristics of the bone is learned in advance using the bone of a normal example as a teacher image.

6. The diagnostic auxiliary image generation apparatus according to claim 5,
wherein the processor is configured to display the diagnostic auxiliary image distinguishably displaying whether the displayed diagnostic auxiliary image is the temporal difference image or the similar difference image.

7. The diagnostic auxiliary image generation apparatus according to claim 5,
wherein the processor is configured to display the diagnostic auxiliary image distinguishably displaying whether the diagnostic auxiliary image is the temporal difference image or the similar difference image or the bone-suppressed image.

8. The diagnostic auxiliary image generation apparatus according to claim 5,
wherein the processor is configured to
perform contrast conversion processing on the diagnostic auxiliary image,
display a diagnostic auxiliary image obtained after contrast conversion of the diagnostic auxiliary image, and
perform different contrast conversion processing according to whether the diagnostic auxiliary image is the temporal difference image or the similar difference image or the bone-suppressed image.

9. The diagnostic auxiliary image generation apparatus according to claim 7,
wherein the processor is configured to perform contrast conversion processing on the diagnostic auxiliary image,
display a diagnostic auxiliary image obtained after contrast conversion of the diagnostic auxiliary image, and
perform different contrast conversion processing according to whether the diagnostic auxiliary image is the temporal difference image or the similar difference image or the bone-suppressed image.

10. The diagnostic auxiliary image generation apparatus according to claim 1,
wherein the processor is configured to determine whether or not the shapes of the organs match each other by determining whether or not lung field shapes and/or rib shapes match each other.

11. The diagnostic auxiliary image generation apparatus according to claim 5,
wherein the processor is configured to
perform a first selection to select normal radiation images in which the subject to be compared with the subject to be diagnosed has the same sex and age range as the subject to be diagnosed,
perform a second selection to select, from the normal radiation images selected by the first selection, normal radiation images including lung field shapes that match a lung field shape of the diagnostic target radiation image,
perform a third selection to select, from the normal radiation images selected by the second selection, normal radiation images including positions of bones overlapping a lung field that matches positions of bones overlapping a lung field in the diagnostic target radiation image,
perform a fourth selection to select, from the normal radiation images selected by the third selection, a normal radiation image including a soft structure similar to a soft structure of the diagnostic target radiation image,
select the normal radiation image having the organ shape that matches the organ shape in the diagnostic target radiation image by the first to fourth selection, and
specify the normal radiation image selected by the fourth selection as a similar case image.

12. The diagnostic auxiliary image generation apparatus according to claim 11,
wherein the bone shape is a shape of a rib or a clavicle.

13. The diagnostic auxiliary image generation apparatus according to claim 11,
wherein the soft structure is a shape of a heart or a pulmonary vessel.

14. The diagnostic auxiliary image generation apparatus according to claim 3,
wherein the processor is configured to perform contrast conversion processing for increasing all pixel values multiple times in a case where the diagnostic auxiliary image is the temporal difference image or a similar difference image, and perform contrast conversion processing for emphasizing pixel values in a low frequency band lower than a specific frequency in a case where the diagnostic auxiliary image is the bone-suppressed image.

15. The diagnostic auxiliary image generation apparatus according to claim 14,
wherein the specific frequency is determined in advance according to a size of a blood vessel included in the chest.

16. A diagnostic auxiliary image generation method in the diagnostic auxiliary image generation apparatus according to claim 1, the method comprising:
a past image search step of searching for the past radiation image, including past organ shape information which is obtained by irradiating the chest of the subject to be diagnosed, from the plurality of radiation images, before the imaging time of the diagnostic target radiation image obtained by irradiating the chest of the subject to be diagnosed;
a determining step of determining whether the search locates the past radiation image;
an acquiring step of acquiring organ shape information from the diagnostic target radiation image;
wherein when it is determined that the search locates the past radiation image, further comparing the shape of the acquired organ shape information of the diagnostic target radiation image with the organ shape information of the past radiation image, and wherein when the shape of the acquired organ shape information matches with the organ shape information of the past radiation image, performing a temporal difference image generation step of generating a temporal difference image as the diagnostic auxiliary image by performing differential processing between the diagnostic target radiation image and the past radiation; and
wherein when it is determined that the search does not locate the past radiation information or when the shape of the acquired organ shape information does not match the organ shape information of the past radiation image, performing a bone-suppressed image generation step of estimating the bone component from the diagnostic target radiation image and generating the bone-suppressed image as the diagnostic auxiliary image by removing the estimated bone component from the diagnostic target radiation image; and
further performing a display step of displaying the diagnostic auxiliary image on the display device,
wherein the temporal difference image that is generated between the past radiation image and the diagnostic target radiation image, satisfies at least:
a degree of matching from a ratio of an area of a product set region of lung field regions to a sum set region of the lung field regions by using superimposed lung field regions of the diagnostic target radiation image and the past radiation image is equal to or greater than a predetermined threshold value, or the degree of matching from the ratio of the area of a product set region of rib regions to a sum set region of the rib regions by using superimposed rib regions of the diagnostic target radiation image and the past radiation image is equal to or greater than a predetermined threshold value,
wherein the bone-suppressed image by removing the estimated bone components from the diagnostic target radiation image, and the estimated bone components is specified estimated the pixel value of the bone component for each pixel, based on bone likeness for each pixel in the diagnostic target radiation image, by using a feature quantity obtained by quantifying characteristics of the bone is learned in advance using the bone of a normal example as a teacher image.

17. A diagnostic auxiliary image generation method in the diagnostic auxiliary image generation apparatus according to claim 5, the method comprising:
a past image search step of searching for the past radiation image, including past organ shape information which is obtained by irradiating the chest of the subject to be diagnosed, from the plurality of radiation images, before the imaging time of the diagnostic target radiation image obtained by irradiating the chest of the subject to be diagnosed;

a determining step of determining whether the search locates the past radiation image;

an acquiring step of acquiring organ shape information from the diagnostic target radiation image;

wherein when it is determined that the search locates the past radiation image, further comparing the shape of the acquired organ shape information of the diagnostic target radiation image with the organ shape information of the past radiation image, and wherein when the shape of the acquired organ shape information matches with the organ shape information of the past radiation image, performing a temporal difference image generation step of generating the temporal difference image as the diagnostic auxiliary image by performing differential processing between the diagnostic target radiation image and the past radiation image; and wherein when it is determined that the search does not locate the past radiation information or when the shape of the acquired organ shape information does not match the organ shape information of the past radiation image, performing a similar image search step of searching for the normal radiation image, which is determined to have the same organ shape by comparing the shape of the organ of the chest appearing on the normal radiation image with the shape of the organ appearing on the diagnostic target radiation image, as a found similar case image and performing a similar difference image generation step of generating the similar difference image as the diagnostic auxiliary image by performing differential processing between the found similar case image and the diagnostic target radiation image;

wherein in a case where it is determined that the search does not locate the past radiation information and in a case where the shape of the acquired organ shape information does not match the organ shape information of the similar case image, said processor estimates a bone component from the diagnostic target radiation image and generates a bone-suppressed image as a diagnostic auxiliary image by removing the estimated bone component from the diagnostic target radiation image, and further performing a display step in which the processor displays the diagnostic auxiliary image on the display device, wherein the temporal difference image that is generated between the past radiation image and the diagnostic target radiation image, satisfies at least:

a degree of matching from a ratio of an area of a product set region of lung field regions to a sum set region of the lung field regions by using superimposed lung field regions of the diagnostic target radiation image and the past radiation image is equal to or greater than a predetermined threshold value, or the degree of matching from the ratio of the area of a product set region of rib regions to a sum set region of rib regions by using superimposed rib regions of the diagnostic target radiation image and the past radiation image is equal to or greater than a predetermined threshold value, wherein the similar difference image is specified by performing differential processing between the found similar case image and the diagnostic target radiation image, and the similar case image is a normal radiation image most similar to the diagnostic target radiation image specified from the following conditions among the stored normal radiation images:

(I) having the same sex and age range as the diagnostic target radiation image;

(II) the degree of matching from the ratio of the area of a product set region of the lung field regions to a sum set region of the lung field regions by using superimposed lung field regions of the diagnostic target radiation image and the past radiation image and the degree of matching from the ratio of the area of a product set region of the rib regions to a sum set region of the rib regions by using superimposed rib regions of the diagnostic target radiation image and the past radiation image;

(III) having a positional relationship between the lung field and the bones overlapping the lung field that is similar to that in the diagnostic target radiation image;

(IV) having a positional relationship between the lung field and the bones overlapping the lung field that is similar to that in the diagnostic target radiation image including a soft structure similar to the soft structure appearing in the diagnostic target radiation image, wherein the bone-suppressed image by removing the estimated bone components from the diagnostic target radiation image, and the estimated bone components is specified estimated pixel value of bone component for each pixel, based on bone likeness for each pixel in the diagnostic target radiation image, by using a feature quantity obtained by quantifying characteristics of the bone is learned in advance using the bone of a normal example as a teacher image.

18. A non-transitory computer readable recording medium recorded with a diagnostic auxiliary image generation program causing a computer to function as the diagnostic auxiliary image generation apparatus according to claim 1, the function comprising:

searching for the past radiation image, including past organ shape information which is obtained by irradiating the chest of the subject to be diagnosed, from the plurality of radiation images, before the imaging time of the diagnostic target radiation image obtained by irradiating the chest of the subject to be diagnosed;

determining whether the search locates the past radiation image;

acquiring organ shape information from the diagnostic target radiation image;

wherein when it is determined that the search locates the past radiation image, further comparing the shape of the acquired organ shape information of the diagnostic target radiation image with the organ shape information of the past radiation image, wherein when the shape of the acquired organ shape information matches with the organ shape information of the past radiation image, generating the temporal difference image as the diagnostic auxiliary image by performing differential processing between the diagnostic target radiation image and the past radiation image; and wherein when it is determined that the search does not locate the past radiation information or when the shape of the acquired organ shape information does not match the organ shape information of the past radiation image, estimating the bone component from the diagnostic target radiation image and generating the bone-suppressed image as the diagnostic auxiliary image by removing the estimated bone component from the diagnostic target radiation image; and
further displaying the diagnostic auxiliary image on the display device,
wherein the temporal difference image that is generated between the past radiation image and the diagnostic target radiation image, satisfies at least:
a degree of matching from a ratio of an area of a product set region of lung field regions to a sum set region of the lung field regions by using superimposed lung field regions of the diagnostic target radiation image and the past radiation image is equal to or greater than a predetermined threshold value, or the degree of matching from the ratio of the area of a product set region of rib regions to a sum set region of the rib regions by using superimposed rib regions of the diagnostic target radiation image and the past radiation image is equal to or greater than a predetermined threshold value,
wherein the bone-suppressed image by removing the estimated bone components from the diagnostic target radiation image, and the estimated bone components is specified estimated the pixel value of the bone component for each pixel, based on bone likeness for each pixel in the diagnostic target radiation image, by using a feature quantity obtained by quantifying characteristics of the bone is learned in advance using the bone of a normal example as a teacher image.

19. A non-transitory computer readable recording medium recorded with a diagnostic auxiliary image generation program causing a computer to function as the diagnostic auxiliary image generation apparatus according to claim 5, the function comprising:
searching for the past radiation image, including past organ shape information which is obtained by irradiating the chest of the subject to be diagnosed, from the plurality of radiation images, before the imaging time of the diagnostic target radiation image obtained by irradiating the chest of the subject to be diagnosed;
storing normal radiation images with no abnormalities among radiation images obtained by irradiating chests of a plurality of subjects to be compared;
generating the temporal difference image as the diagnostic auxiliary image by performing differential processing between the diagnostic target radiation image and the past radiation image; and
wherein when it is determined that the search does not locate the past radiation information or when the shape of the acquired organ shape information does not match the organ shape information of the past radiation image, searching for the normal radiation image, which is determined to have the same organ shape by comparing the shape of the organ of the chest appearing on the normal radiation image with the shape of the organ appearing on the diagnostic target radiation image, as the similar case image,
wherein in a case where it is determined that the search does not locate the past radiation information and in a case where the shape of the acquired organ shape information does not match the organ shape information of the similar case image, said processor estimates a bone component from the diagnostic target radiation image and generates a bone-suppressed image as a diagnostic auxiliary image by removing the estimated bone component from the diagnostic target radiation image, and generating the similar difference image as the diagnostic auxiliary image by performing differential processing between the found similar case image and the diagnostic target radiation image; and
further displaying the diagnostic auxiliary image on the display device,
wherein the temporal difference image that is generated between the past radiation image and the diagnostic target radiation image, satisfies at least:
a degree of matching from a ratio of an area of a product set region of lung field regions to a sum set region of the lung field regions by using superimposed lung field regions of the diagnostic target radiation image and the past radiation image is equal to or greater than a predetermined threshold value, or the degree of matching from the ratio of the area of a product set region of rib regions to a sum set region of the rib regions by using superimposed rib regions of the diagnostic target radiation image and the past radiation image is equal to or greater than a predetermined threshold value,
wherein the similar difference image is specified by performing differential processing between the found similar case image and the diagnostic target radiation image, and the similar case image is a normal radiation image most similar to the diagnostic target radiation image specified from the following conditions among the stored normal radiation images:
(I) having the same sex and age range as the diagnostic target radiation image;
(II) the degree of matching from the ratio of the area of a product set region of the lung field regions to a sum set region of the lung field regions by using superimposed lung field regions of the diagnostic target radiation image and the past radiation image and the degree of matching from the ratio of the area of a product set region of the rib regions to a sum set region of the rib regions by using superimposed rib regions of the diagnostic target radiation image and the past radiation image;
(III) having a positional relationship between the lung field and the bones overlapping the lung field that is similar to that in the diagnostic target radiation image;
(IV) having a positional relationship between the lung field and the bones overlapping the lung field that is similar to that in the diagnostic target radiation image including a soft structure similar to the soft structure appearing in the diagnostic target radiation image,
wherein the bone-suppressed image by removing the estimated bone components from the diagnostic target radiation image, and the estimated bone components is specified estimated pixel value of bone component for each pixel, based on bone likeness for each pixel in the diagnostic target radiation image, by using a feature quantity obtained by quantifying characteristics of the bone is learned in advance using the bone of a normal example as a teacher image.

20. The diagnostic auxiliary image generation apparatus according to claim 1,
wherein the processor is configured to
determine whether or not the shapes of the organs match each other by determining whether or not lung field shapes match each other, and determine that the shapes of the organs do not match each other in a case where the lung field shapes do not match each other, and determine whether or not the shapes of the organs match each other by determining whether or not rib shapes match each other in a case where the lung field shapes match each other.

21. The diagnostic auxiliary image generation apparatus according to claim 1, wherein in a case of the diagnostic auxiliary image is a temporal difference image, the diagnostic auxiliary image is performed contrast conversion processing for emphasis by increasing all the pixel values multiple times, or in a case of the diagnostic auxiliary image is a bone-suppressed image, the diagnostic auxiliary image is performed contrast conversion processing for emphasizing pixel values in a low frequency band lower than a specific frequency.

22. The diagnostic auxiliary image generation apparatus according to claim 5, wherein in a case of the diagnostic auxiliary image is a temporal difference image or a similar difference image, the diagnostic auxiliary image is performed contrast conversion processing for emphasis by increasing all the pixel values multiple times, or in a case of the diagnostic auxiliary image is a bone-suppressed image, the diagnostic auxiliary image is performed contrast conversion processing for emphasizing pixel values in a low frequency band lower than a specific frequency.

23. The diagnostic auxiliary image generation method in the diagnostic auxiliary image generation apparatus according to claim 16, wherein in a case of the diagnostic auxiliary image is a temporal difference image, the diagnostic auxiliary image is performed contrast conversion processing for emphasis by increasing all the pixel values multiple times, or in a case of the diagnostic auxiliary image is a bone-suppressed image, the diagnostic auxiliary image is performed contrast conversion processing for emphasizing the pixel values in a low frequency band lower than a specific frequency.

24. The diagnostic auxiliary image generation method in the diagnostic auxiliary image generation apparatus according to claim 17, wherein in a case of the diagnostic auxiliary image is a temporal difference image or a similar difference image, the diagnostic auxiliary image is performed contrast conversion processing for emphasis by increasing all the pixel values multiple times, or in a case of the diagnostic auxiliary image is a bone-suppressed image, the diagnostic auxiliary image is performed contrast conversion processing for emphasizing the pixel values in a low frequency band lower than a specific frequency.

25. The non-transitory computer readable recording medium recorded with a diagnostic auxiliary image generation program causing a computer to function as the diagnostic auxiliary image generation apparatus according to claim 18, wherein in a case of the diagnostic auxiliary image is a temporal difference image, the diagnostic auxiliary image is performed contrast conversion processing for emphasis by increasing all the pixel values multiple times, or in a case of the diagnostic auxiliary image is a bone-suppressed image, the diagnostic auxiliary image is performed contrast conversion processing for emphasizing the pixel values in a low frequency band lower than a specific frequency.

26. The non-transitory computer readable recording medium recorded with a diagnostic auxiliary image generation program causing a computer to function as the diagnostic auxiliary image generation apparatus according to claim 19, wherein in a case of the diagnostic auxiliary image is a temporal difference image or a similar difference image, the diagnostic auxiliary image is performed contrast conversion processing for emphasis by increasing all the pixel values multiple times, or in a case of the diagnostic auxiliary image is a bone-suppressed image, the diagnostic auxiliary image is performed contrast conversion processing for emphasizing the pixel values in a low frequency band lower than a specific frequency.

* * * * *